(12) United States Patent (10) Patent No.: US 8,669,522 B2
Yamaguchi et al. (45) Date of Patent: Mar. 11, 2014

(54) MASK INSPECTION APPARATUS AND MASK INSPECTION METHOD

(75) Inventors: Shinji Yamaguchi, Tokyo (JP); Masato Naka, Kanagawa-ken (JP); Hiroyuki Kashiwagi, Kanagawa-ken (JP); Masamitsu Itoh, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 195 days.

(21) Appl. No.: 13/416,282

(22) Filed: Mar. 9, 2012

(65) Prior Publication Data

US 2012/0241645 A1 Sep. 27, 2012

(30) Foreign Application Priority Data

Mar. 25, 2011 (JP) ................................ 2011-067630

(51) Int. Cl.
*H01J 37/28* (2006.01)
(52) U.S. Cl.
USPC ........................... 250/305; 250/307; 250/310
(58) Field of Classification Search
USPC ......................................................... 250/305
See application file for complete search history.

(56) References Cited

U.S. PATENT DOCUMENTS

| | | | | |
|---|---|---|---|---|
| 4,748,327 A | * | 5/1988 | Shinozaki et al. | ......... 250/358.1 |
| 2004/0243320 A1 | * | 12/2004 | Chang et al. | .................... 702/30 |
| 2010/0218287 A1 | | 8/2010 | Nakata et al. | |
| 2010/0315643 A1 | | 12/2010 | Kashiwagi et al. | |
| 2010/0320171 A1 | * | 12/2010 | Mao et al. | ....................... 216/65 |

FOREIGN PATENT DOCUMENTS

| | | |
|---|---|---|
| JP | 11-37957 | 2/1999 |
| JP | 2005-512339 | 4/2005 |
| JP | 2005-257339 | 9/2005 |
| JP | 2008-96252 | 4/2008 |
| JP | 2010-197208 | 9/2010 |
| JP | 2010-197347 | 9/2010 |
| JP | 2010-286309 | 12/2010 |

OTHER PUBLICATIONS

Notification of Reason(s) for Refusal issued by the Japanese Patent Office on Apr. 26, 2013, for Japanese Patent Application No. 2011-067630, and English-language translation thereof.

* cited by examiner

*Primary Examiner* — Phillip A Johnston
(74) *Attorney, Agent, or Firm* — Finnegan, Henderson, Farabow, Garrett & Dunner, L.L.P.

(57) ABSTRACT

According to one embodiment, a mask inspection apparatus includes a decompression chamber, a holder, a light irradiation unit, a detection unit, an electrode, and a control unit. The holder is provided in the decompression chamber and holds a mask. The light irradiation unit irradiates a major surface of the mask held by the holder with a light. The detection unit is provided in the decompression chamber to detect electrons generated when the major surface of the mask is irradiated with the light. The electrode is provided between the holder and the detection unit and guides the electrons in a direction from the holder toward the detection unit. The control unit compares a detection result of the electrons detected by the detection unit with a reference value.

19 Claims, 15 Drawing Sheets

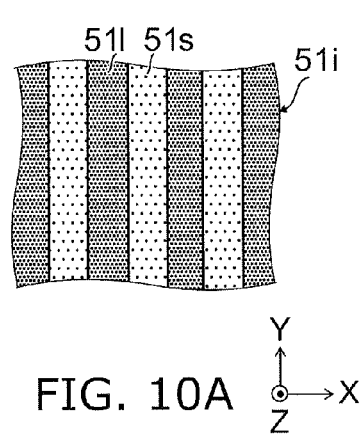
FIG. 10A
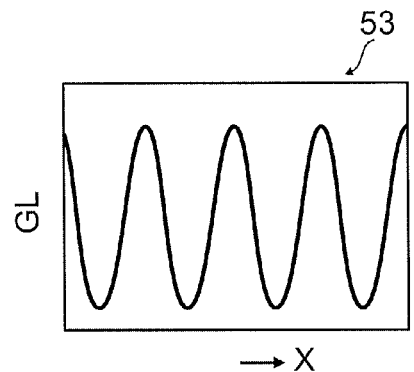
FIG. 10B
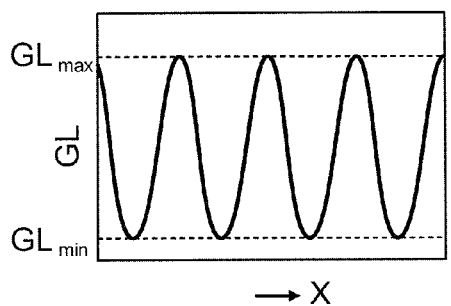
FIG. 10C
| θ (degrees) | GLP= $(GL_{max}-GL_{min})/(GL_{max}+GL_{min})$ |
|---|---|
| 0 | 0.4 |
| 5 | 0.5 |
| 10 | 0.7 |
| 15 | 0.9 |
| 20 | 0.8 |
| 25 | 0.7 |
| ⋮ | ⋮ |
| 55 | 0.5 |
| 60 | 0.4 |
| 65 | 0.3 |
| 70 | 0.1 |
FIG. 10D

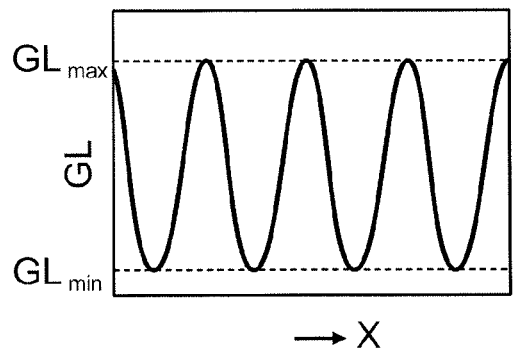
FIG. 15A
| λ | GLP= (GL$_{max}$- GL$_{min}$)/(GL$_{max}$+GL$_{min}$) |
|---|---|
| 199 (i = 1) | 0.2 |
| 257 (i = 2) | 0.4 |
| 266 (i = 3) | 0.7 |
| 355 (i = 4) | 0.4 |
| 488 (i = 7) | 0.2 |
| 514 (i = 8) | 0.15 |
| 532 (i = 5) | 0.11 |
| 633 (i = 9) | 0.1 |
| 1064 (i = 6) | 0.09 |
FIG. 15B
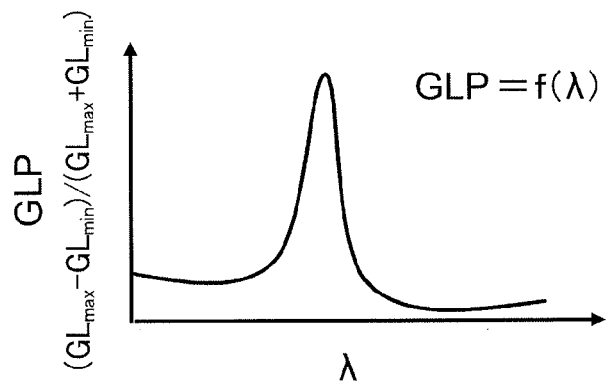
FIG. 15C

MASK INSPECTION APPARATUS AND MASK INSPECTION METHOD

CROSS-REFERENCE TO RELATED APPLICATIONS

This application is based upon and claims the benefit of priority from the prior Japanese Patent Application No. 2011-067630, filed on Mar. 25, 2011; the entire contents of which are incorporated herein by reference.

FIELD

Embodiments described herein relate generally to a mask inspection apparatus and a mask inspection method.

BACKGROUND

A mask is used, for example, in lithography of manufacture of a semiconductor device. As the semiconductor device becomes smaller, a concave-convex pattern provided in the mask is also made smaller. The configuration for inspecting a mask having a fine concave-convex pattern, with a high sensitivity is desired.

BRIEF DESCRIPTION OF THE DRAWINGS

FIGS. 10A to 10D are schematic views illustrating the operations of the mask inspection apparatus according to the first embodiment;

FIGS. 15A to 15C are schematic views illustrating another operation of the mask inspection apparatus according to the first embodiment;

DETAILED DESCRIPTION

Figure 1:
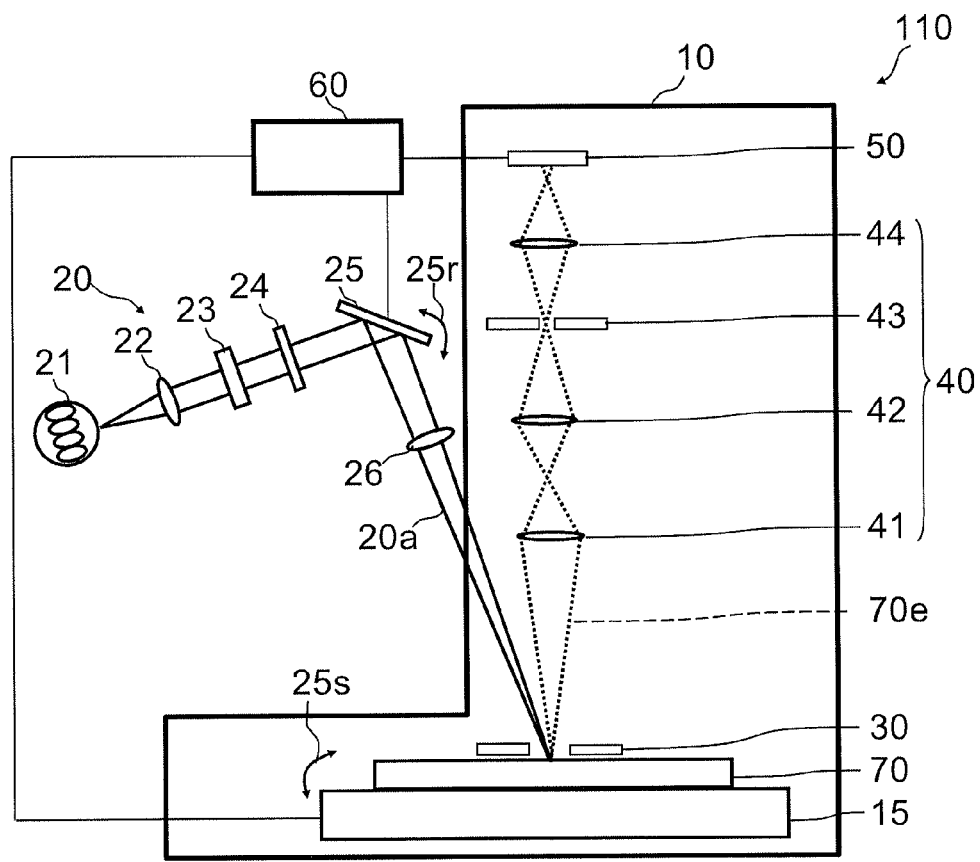
FIG. 1 is a schematic view illustrating the configuration of a mask inspection apparatus according to a first embodiment.

According to one embodiment, a mask inspection apparatus includes a decompression chamber, a holder, a light irradiation unit, a detector, an electrode, and a controller. The holder is provided in the decompression chamber and holds a mask. The light irradiation unit irradiates a major surface of the mask held by the holder with a light. The detector is provided in the decompression chamber to detect electrons generated when the major surface of the mask is irradiated with the light. The electrode is provided between the holder and the detector and guides the electrons in a direction from the holder toward the detector. The controller compares a detection result of the electrons detected by the detector with a reference value.

According to another embodiment, a mask inspection method is disclosed. The method can include an inspection process. The inspection process can include detecting electrons generated when a major surface of a mask disposed in a reduced pressure atmosphere is irradiated with a light, the electrons being guided with an electrode. The inspection process includes comparing a detection result of the detected electrons with a reference value.

Various embodiments will be described hereinafter with reference to accompanying drawings.

The drawings are schematic or conceptual; and the relationships between the thicknesses and widths of portions, the proportions of sizes among portions, etc., are not necessarily the same as the actual values thereof. Furthermore, the dimensions and the proportions may be illustrated differently among the drawings, even for identical portions.

In the specification and the drawings of the application, components similar to those described in regard to a drawing thereinabove are marked with like reference numerals, and a detailed description is omitted as appropriate.

First Embodiment

FIG. 1 is a schematic view illustrating the configuration of a mask inspection apparatus according to a first embodiment.

As shown in FIG. 1, the mask inspection apparatus 110 according to the embodiment includes: a decompression chamber 10; a holder 15; a light irradiation unit 20; a detector 50, an electrode 30; and a controller 60.

The decompression chamber 10 can maintain its inside at an atmospheric pressure lower than the pressure of ambient.

The holder 15 is provided in the decompression chamber 10. The holder 15 holds a mask 70. As the holder 15, a substrate stage (for example, X-Y stage etc.) is used. The mask 70 is placed on the holder 15. The mask 70 has a concave-convex pattern provided on the major surface of the mask 70. The mask 70 is used, for example, in lithography of manufacture of a semiconductor device etc. However, in the embodiment, use application of the mask 70 is arbitrary. The mask 70 is, for example, an EUV mask. Examples of the mask 70 will be described later.

The light irradiation unit 20 irradiates the major surface of the mask 70 held by the holder 15, with light 20a. The light irradiation unit 20 includes, for example, a light source 21. The light source 21 generates the light 20a with which the mask 70 is to be irradiated. The wavelength of the light 20a is, for example, 257 nanometers (nm). However, the example is not limited to this, as the light 20a, light having wavelength of, for example, not less than 199 nm and not more than 1064 nm can be used.

The light irradiation unit 20 can furthermore include, for example, an angle changing unit 25. In this example, a mirror is used as the angle changing unit 25. By using the angle changing unit 25, the incident angle of the light 20a into the major surface of the mask 70 can be changed.

The light irradiation unit 20 can further includes a light source lens 22, a polarizing element 23 (polarizing prism etc.), a wavelength plate 24, and a condensing lens 26. The light generated by the light source 21 is controlled by these optical elements, and the mask 70 is irradiated with the light 20a having a suitable spot size. Furthermore, as described later, the mask 70 is irradiated with the light 20a having suitable polarization properties.

In addition, at least a part of the elements included in the light irradiation unit 20 may be provided inside the decompression chamber 10. Furthermore, at least a part of the elements included in the light irradiation unit 20 may be provided outside the decompression chamber 10. The light 20a from the light irradiation unit 20 may be guided into the decompression chamber 10 via, for example, a window part (not shown) provided to the decompression chamber 10, and thus the mask 70 may be irradiated with the light 20a.

The detector 50 is provided inside the decompression chamber 10. The detector 50 detects electrons (photoelectrons 70e) generated from the major surface of the mask 70 irradiated with the light 20a. The photoelectrons 70e will be described later. As the detector 50, for example, a TDI (Time Delayed Integration system) sensor etc. is used. The detector 50 can detect, for example, the photoelectrons 70e, as an image.

The electrodes 30 are provided between the holder 15 and the detector 50 in the decompression chamber 10. Specifically, the electrodes 30 are provided between the mask 70 held by the holder 15 and the detector 50. The electrodes 30 guide the photoelectrons 70e from the holder 15 toward the detector 50. A voltage is applied between, for example, the holder 15 and each of the electrodes 30. A potential difference is generated by the voltage between the holder 15 and each of the electrodes 30, and the photoelectrons 70e generated from the major surface 70 are drawn out from the mask 70, accelerated and guided toward the detector 50. Because of this, the generated photoelectrons 70e enter into the detector 50 efficiently.

The controller 60 compares a result detected by the detector 50 with a reference value. The controller 60 is connected to, for example, the detector 50. The detection data (for example, image data) regarding the photoelectrons 70e obtained by the detector 50 is supplied to the controller 60. The controller 60 compares the supplied detection data with the reference value, and inspects the mask 70 based on the result.

As the reference value, a value suitable for inspection is used. The reference value will be described later.

In the specific example, a detection side optical unit 40 is provided between the holder 15 and the detector 50. The detection side optical unit 40 includes, for example, an objective lens 41 provided between the holder 15 and the detector 50, an intermediate lens 42 provided between the objective lens 41 and the detector 50, an NA aperture 43 provided between the intermediate lens 42 and the detector 50, and a projector lens 44 provided between the NA aperture 43 and the detector 50.

The detection side optical unit 40 can include a first aperture with a first numerical aperture, and a second aperture with a second numerical aperture different from the first numerical aperture. Because of this, the mask 70 can be irradiated with beams of light 20a with different illumination shapes.

Figure 2A:
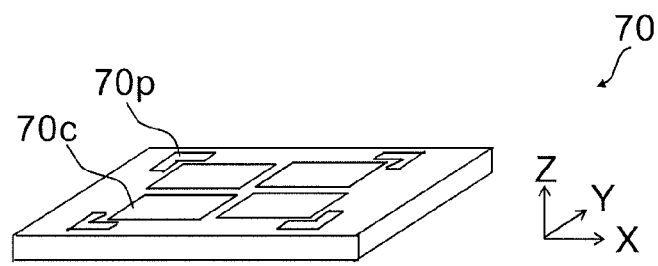
FIGS. 2A to 2C are schematic views illustrating the configuration of a mask inspected by the mask inspection apparatus according to the first embodiment.
Figure 2B:
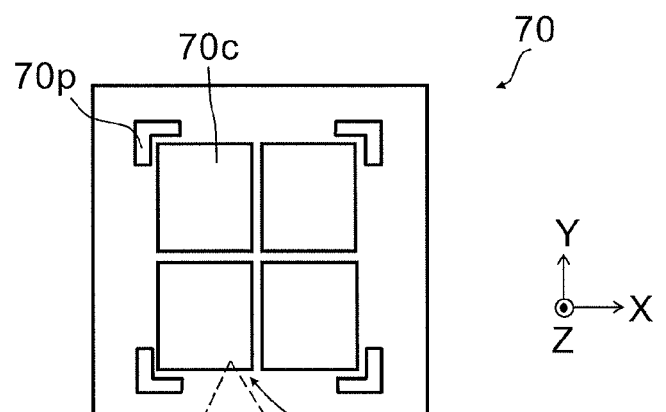
Figure 2C:
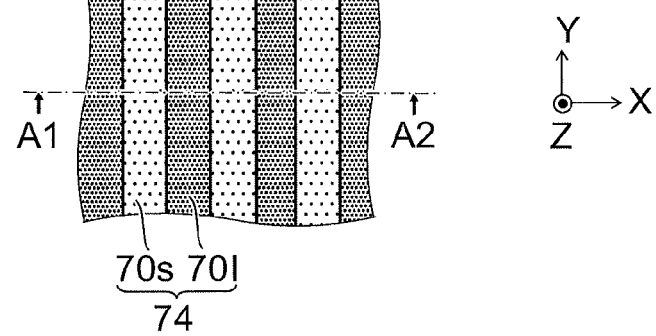

FIGS. 2A to 2C are schematic views illustrating the configuration of a mask inspected by the mask inspection apparatus according to the first embodiment.

FIG. 2A is a perspective view, and FIG. 2B is a plan view. FIG. 2C is an enlarged plan view illustrating a part in FIG. 2B (section A).

As shown in FIGS. 2A and 2B, the mask 70 has a pattern part 70c and a circumference mark part 70p provided around the pattern part 70c.

As shown in FIG. 2C, a concave-convex pattern 74 is provided to the pattern part 70c. In the example, as the concave-convex pattern 74 in the pattern part 70c, belt-like line parts 70l and space parts 70s between two of the line parts are provided. However, in the embodiment, the plane pattern of the concave-convex pattern 74 is arbitrary. For example, the concave-convex pattern 74 may also have a pattern like a polygonal hole, a circular hole, or a pillar. Hereinafter, a case in which the concave-convex pattern 74 is a belt-like pattern having lines and spaces, will be described.

Figure 3:
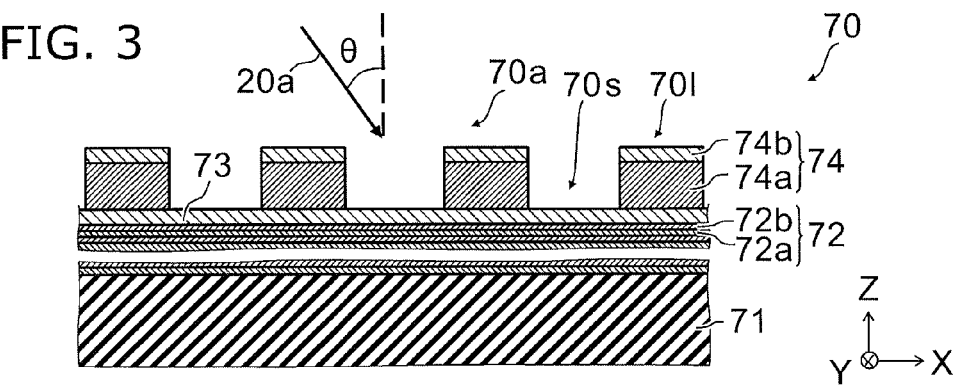
FIG. 3 is a schematic cross-sectional view illustrating the configuration of a mask inspected by the mask inspection apparatus according to the first embodiment.

FIG. 3 is a schematic cross-sectional view illustrating the configuration of a mask inspected by the mask inspection apparatus according to the first embodiment.

That is, FIG. 3 is a cross-sectional view along A1-A2 line in FIG. 2C.

As shown in FIG. 3, the mask 70 has, for example, a quartz substrate 71, a multilayer film 72 provided on the substrate 71, a metal film 73 provided on the multilayer film 72, and the concave-convex pattern 74 provided on the metal film 73.

The multilayer film 72 has, for example, Mo films 72a and Si films 72b, which are alternately stacked each other. The thickness of the Mo film 72a is, for example, 3 nm. The thickness of the Si film 72b is, for example, 4 nm. For example 40 pairs of the Mo film 72a and the Si film 72 are stacked.

As the metal film 73, for example, a Ru film is used. The thickness of the metal film 73 is, for example, 2 nm.

The concave-convex pattern 74 has, for example, a TaBN film 74a provided on the metal film 73, and a TaBO film 74b provided on the TaBN film 74a. When the concave-convex pattern 74 has lines and spaces, the half pitch of the concave-convex pattern 74 is, for example, not less than about 40 nm and not more than about 100 nm. However, in the embodiment, the pitch of the concave-convex pattern 74 is not limited to this and is arbitrary. In the mask 70, a surface, on which the concave-convex pattern 74 is provided, is the major surface 70a.

The light 20a enters such a mask 70. The incident angle θ of the light 20a is an angle between the normal line of the major surface 70a of the mask 70 and the light 20a.

Figure 4A:
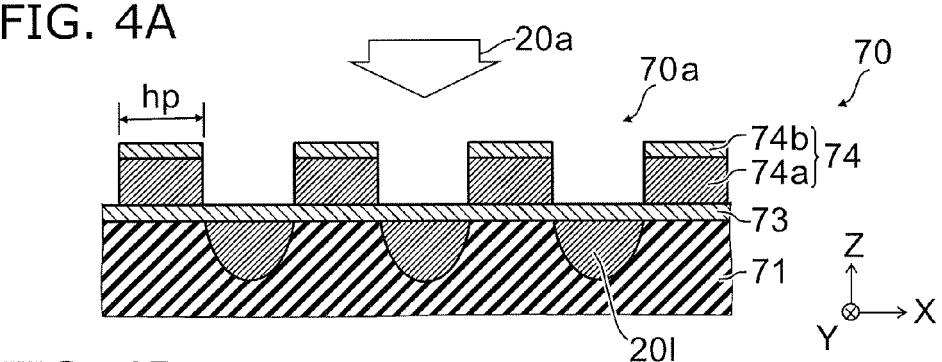
FIGS. 4A and 4B are schematic cross-sectional views illustrating the operation of the mask inspection apparatus according to the first embodiment.
Figure 4B:
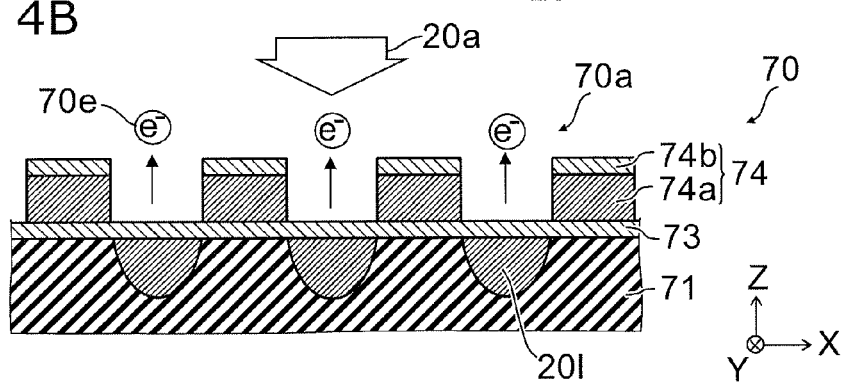

FIGS. 4A and 4B are schematic cross-sectional views illustrating the operation of the mask inspection apparatus according to the first embodiment.

As shown in FIG. 4A, in mask inspection apparatus according to the embodiment, the major surface 70a of the mask 70 is irradiated with the light 20a from the light irradiation unit 20. The half pitch hp (line width or space width of the lines and spaces) of the concave-convex pattern 74 of the mask 70 is shorter than the wavelength λ (for example, 275 nm) of the light 20a. The half pitch hp is, for example, not more than 100 nm. At this time, near the pattern edge (edge portion) of each of the plurality of concave-convex patterns 74, near-field light 20l is generated. The near-field light 20l is not influenced by a diffraction limit. For this reason, even when the half pitch hp of the concave-convex pattern 74 is shorter than the wavelength λ of the light 20a, the near-field light 20l depending on the concave-convex pattern 74 can also be obtained. The near-field light 20l is distributed in a shape depending on a minute opening (for example, a space part 70s) of the concave-convex pattern 74.

As shown in FIG. 4B, the photoelectrons 70e excited by the near-field light 20l described above is generated. In the mask inspection apparatus 110, the photoelectrons 70e are detected by the detector 50. Then, the detection result of the photoelectrons 70e is compared with a reference value by the controller 60.

Figures 5A, 5B:
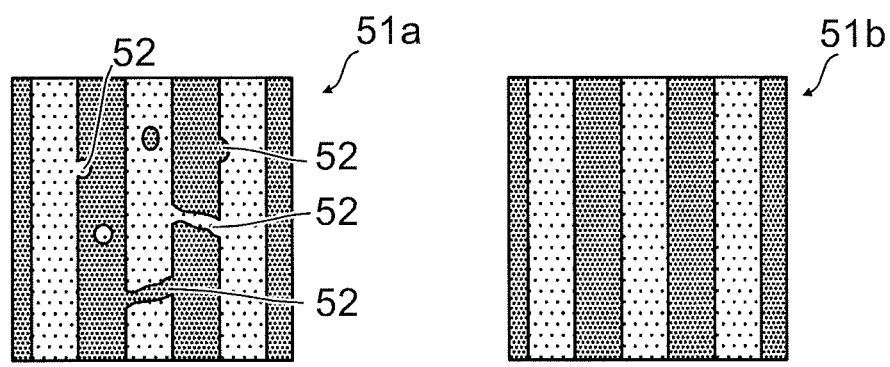
FIGS. 5A and 5B are schematic cross-sectional views illustrating the operation of the mask inspection apparatus according to the first embodiment.

FIGS. 5A and 5B are schematic cross-sectional views illustrating the operation of the mask inspection apparatus according to the first embodiment.

FIG. 5A illustrates the detection image of the photoelectrons 70e obtained by the detector 50. For this case, a pattern abnormality 52 such as a structural error of the concave-convex pattern 74 or a foreign matter pattern on the concave-convex pattern 74 is observed in the detection image. Such a pattern abnormality 52 is determined as a defect. For the determination for repairing such a defect or removing the defect through the use of a cleaning technique etc., the mask inspection apparatus 110 according to the embodiment is used. At this time, the detection image (detection data) of the photoelectrons 70e obtained by the detector 50 is compared with a reference value.

FIG. 5B illustrates a reference image corresponding to the reference value. The controller 60 compares the reference image (data) illustrated in FIG. 5B with the detection image (data) illustrated in FIG. 5A. The mask 70 is inspected based on the result.

Depending on a value used as the reference value (data or image), inspection such as Cell to cell comparison checking, Die to die comparison checking, or Die to database comparison checking, is performed.

In this way, in the mask inspection apparatus 110 according to the embodiment, inspection of the defect in the mask 70 with the concave-convex pattern 74, of which half pitch hp is shorter than the wavelength λ of the light 20a to be used, is performed by detecting photoelectrons 70e excited by the near-field light 20l based on the light 20a.

In a reference example, in which a mask with a pattern of not more than 100 nm for use in, for example, short wavelength EUV lithography is irradiated with light, and reflection light reflected by the mask is directly inspected, an image reflecting the mask pattern cannot be obtained, because the pattern size is not more than the diffraction limit. For this reason, it is difficult to inspect such a fine pattern by this technique.

In contrast, a technique, in which such a fine pattern is irradiated with electrons, and electrons obtained from the mask are detected, can also be considered. The inventors have tried to inspect a mask as described above by using an inspection apparatus to which such a technique is applied. As a result of the inspection using the inspection apparatus with this configuration under various experimental conditions, it has been confirmed that accuracy of mask inspection is low, because many noises were observed in the inspection image, leading to the difficulty of distinguishing the noises from signals of desired defects.

The inventors have tried to cause such an apparatus to irradiate the mask 70 that is an object to be inspected with light. As a result, it has been found out that a clear pattern depending on the concave-convex pattern 74 of the mask 70 is obtained in the inspection image (image of the photoelectrons 70e) obtained when the mask 70 is irradiated with light. It has been confirmed that the inspection image (image of the photoelectrons 70e) is an image corresponding to the photoelectrons 70e excited by the near-field light 20l generated depending on the concave-convex pattern 74 of the mask 70.

Based on the above-described phenomenon found out by the inventors, the configuration of the mask inspection apparatus 110 according to the embodiment is constructed. That is, in the mask inspection apparatus 110, the light irradiation unit 20 irradiating the mask 70 that is an inspection object with the light 20a, the electrodes 30 for accelerating the photoelectrons 70e excited by the near-field light 20l generated in the mask 70 to guide them toward the detector 50, and the detector 50 for detecting the photoelectrons 70e, are provided. In addition, the decompression chamber 10 for maintaining the mask 70, the electrodes 30, and the detector 50 at a reduced pressure during the inspection is provided. Such the configuration enables to detect photoelectrons 70e excited by the near-field light 20l based on the light 20a to be radiated on the mask 70.

In addition, there is a scanning probe microscope for observing a sample using a near-field light. In considering to use the scanning probe microscope for mask inspection, when a large inspection area on the mask is inspected, it is difficult to generate uniform near-field light due to wearing of the probe. Therefore, this configuration is not suitable for mask inspection.

In contrast, in the embodiment, since the configuration, in which the mask 70 is irradiated with the light 20a, and the photoelectrons 70e generated via the near-field light 20l, is used, the uniform near-field light 20l may be obtained stably. For this reason, the embodiment can be applied suitably for mask inspection, and a mask with a minute pattern can be inspected in high accuracy.

Figure 6A:
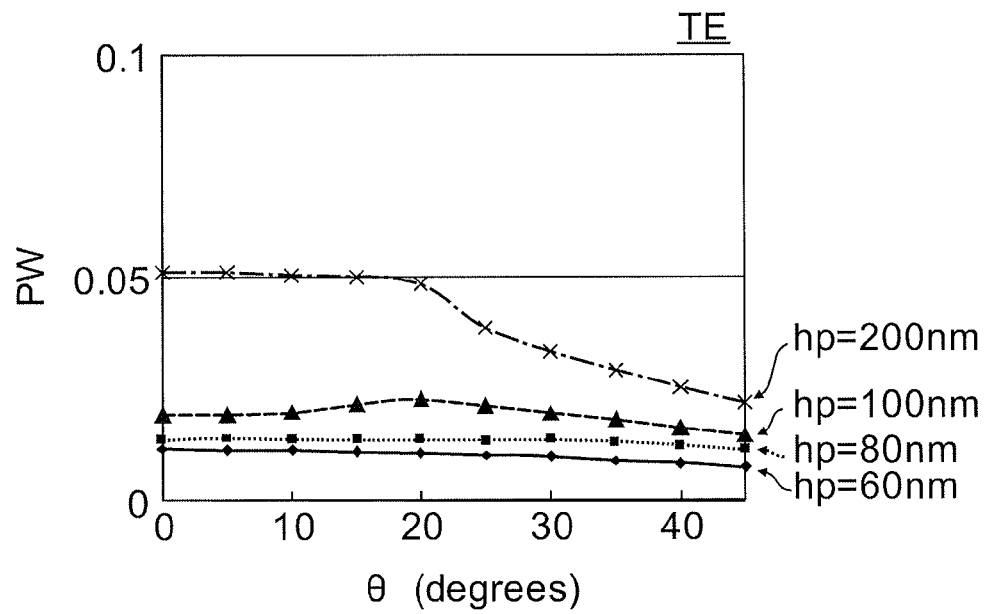
FIGS. 6A and 6B are graph charts illustrating the characteristics of the mask inspection apparatus according to the first embodiment.
Figure 6B:
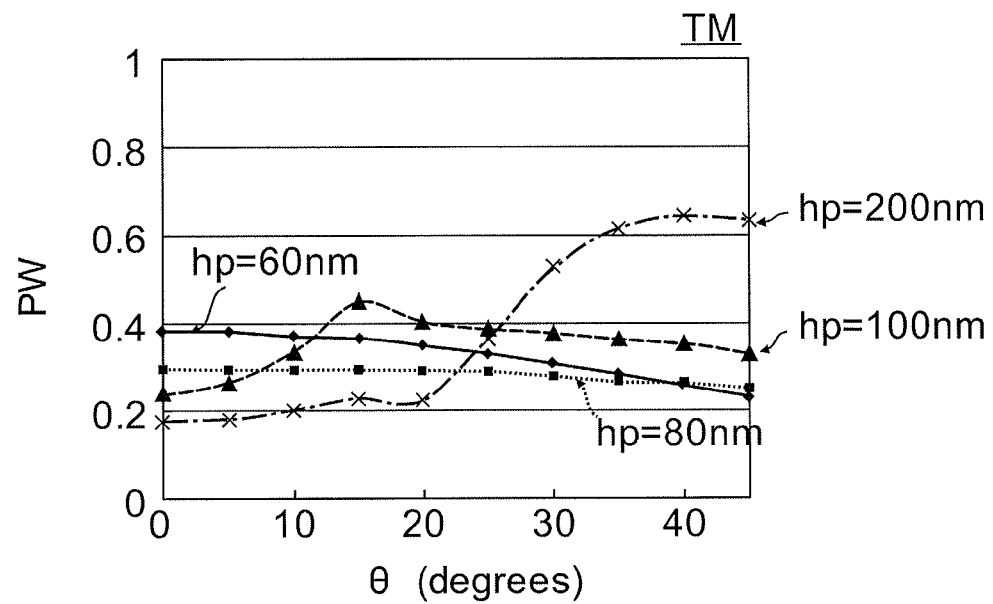

FIGS. 6A and 6B are graph charts illustrating the characteristics of the mask inspection apparatus according to the first embodiment.

These drawings illustrate the simulation results of the properties of the near-field light 20l generated when the mask 70 is irradiated with the light 20a. For the simulation, in the configuration of the mask 70 illustrated in FIG. 3, the power PW of the near-field light 20l generated at the position of the metal film 73 (for example, Ru film) is calculated when the half pitch hp of the concave-convex pattern 74 was changed to be 60 nm, 80 nm, 100 nm, and 200 nm. The horizontal axis represents the incident angle θ, and the vertical axis represents the power PW (relative value). FIG. 6A illustrates the result for a case of the TE polarization light 20a irradiation, and the FIG. 6B illustrates the result for a case of the TM polarization light 20a irradiation. The wavelength λ of the light 20a is 257 nm.

As shown in FIG. 6A, for a case of TE polarization, the power PW of the near-field light 20l is about 0.05 (5%) at the maximum.

In contrast, as shown in FIG. 6B, for a case of TM polarization, the power PW of the near-field light 20l is not less than 0.2 (20%).

Because of this, by using TM polarized light as the light 20a with which the major surface 70a of the mask 70 is irradiated, the power PW of the near-field light 20l generated in the concave-convex pattern 74 is easily made large. In addition, the conversion efficiency to the photoelectrons 70e becomes high. Because of this, in the mask inspection apparatus 110 according to the embodiment, it is desirable that the light 20a includes a TM polarization component.

For example, when the concave-convex pattern 74 includes a hole shape, circularly polarized light including a TM polarization component or elliptically polarized light including a TM polarization component may be used. The electric field Ex in x-direction and the electric field Ey in y-direction are represented as follows.

$$Ex = a \cdot \cos(kz - \omega t)$$

$$Ey = a \cdot \cos(kz - \omega t - \pi/2)$$

In the case of circularly polarized light, the phase difference between the electric field Ex and the electric field Ey is kept at $\pi/2$, and following formula is satisfied.

$$Ex^2 + Ey^2 = a^2$$

That is, when circularly polarized light is used, TM polarization components can be obtained in all directions of the concave-convex pattern 74. The use of circularly polarized light as the light 20a is one of preferable conditions.

In addition, it is also possible to use combination of TM polarized light and circularly polarized light so as to improve sensitivity and accuracy of defect detection. Especially, when the half pitch hp is shorter than 60 nm, it is effective to use combination of TM polarized light and circularly polarized light. Furthermore, the sensitivity of defect detection can be improved by adjusting incident polarized light and combination of polarized light depending on at least any of the concave-convex pattern 74 and a signal desired to be detected.

Furthermore, as shown in FIG. 6B, when the half pitch hp is 60 nm, the power PW of the near-field light 20l becomes its maximum value for the incident angle θ of 0°, and as the incident angle θ becomes larger, the power PW becomes smaller. When the half pitch hp is 80 nm, the power PW of the near-field light 20l becomes substantially constant for the incident angle θ of 0° to 20°, and as the incident angle θ becomes larger than 20°, the power PW becomes smaller. When the half pitch hp is 100 nm, the power PW of the near-field light 20l becomes its maximum value for the incident angle θ of 15°. When the half pitch hp is 200 nm, the power PW of the near-field light 20l becomes its maximum value for the incident angle θ of about 40°.

In this way, incident angle θ changes, at which the power PW of the near-field light 20l becomes the largest depending on the specifications (for example, the half pitch hp etc.) of the concave-convex pattern 74s. For this reason, in the mask inspection apparatus 110 according to the embodiment, the incident angle θ can be changed depending on the specification of the mask 70 of the inspection object. Because of this, more suitable (for example, higher sensitivity and higher-accuracy) inspection can be achieved. The change of the incident angle θ is performed by, for example, an angle changing unit 25. For example, as the angle changing unit 25, a mirror included in the light irradiation unit 20 can be used.

For example, as shown in FIG. 1, the incident angle θ can be changed by changing the angle of the mirror (angle changing unit 25) as illustrated by an arrow 25r. That is, the light irradiation unit 20 changes the incident angle θ of the irradiation light 20a relative to the major surface of the mask 70. Furthermore, as illustrated by the arrow 25r, the angle of the mask 70 may be changed. In this case, the holder acts as an incident angle changing unit. The holder 15 can change the angle of the mask 70 so that an angle ((incident angle θ) between the radiating light 20a and the major surface of the mask 70 may change. Because of this, the mask inspection apparatus 110 can further include the angle changing unit 25 for changing the incident angle θ relative to the major surface 70a of the light 20a. In addition, for example, the holder 15 may change the incident angle θ relative to the major surface 70a of the light 20a.

Moreover, in some cases, a plurality of kinds of patterns are provided in the major surface 70a of the mask. For example, four kinds of concave-convex patterns 74 of which half pitch hp is 60 nm, 80 nm, 100 nm, and 200 nm may be provided in the major surface 70a of the mask 70. In this case, the incident angle θ is set to be not less than 20° and not more than 30°. Because of this, a large power PW can be obtained in each of four kinds of the concave-convex patterns 74. That is, in this case, a suitable condition for the incident angles θ is a condition of not less than 20° and not more than 30°.

In contrast, three kinds of concave-convex patterns 74 of which half pitch hp is 60 nm, 80 nm, and 100 nm may be provided in the major surface 70a of the mask 70. In this case, the incident angle θ is set to be not less than 10° and not more than 20°. Because of this, a large power PW is obtained in each of three kinds of the concave-convex patterns 74. That is, in this case, a suitable condition for the incident angles θ is a condition of not less than 10° and not more than 20°. Under this condition, the average of the power PW of the near-field light 20l becomes large. By using an incident angle θ having a large average of the power PW, more suitable inspection can be performed.

In this way, in the mask inspection apparatus 110, inspection can be performed by using an incident angle θ having a large power PW, based on simulation result of the power PW of the near-field light 20l for the specification of a specific concave-convex pattern 74. For example, for a case in which the half pitch hp is 100 nm, from a simulation result, it is estimated that the power PW of the near-field light 20l becomes large under a condition in which the incident angles θ is not less than 10° and not more than 20°. Based on the result, it is possible to cause the light 20a to enter the major surface 70a of the mask 70 at an incident angle θ of not less than 10° and not more than 20°. Because of this, more suitable inspection can be performed.

In addition, inspection can be performed using an incident angle θ having a total large power PW, based on simulation result of the power PW of the near-field light 20l for a plurality kinds of specification of the concave-convex pattern 74. As a condition in which total power PW becomes large, a condition in which the average of the power PW in a plurality of kinds of specifications becomes large, can be used. Furthermore, as a condition in which total power PW becomes large, a condition in which values of the power PW in a plurality kinds of specifications become uniform (for example, the standard deviation becomes small), can also be used.

Furthermore, for a specific specification of the concave-convex pattern 74, inspection can be performed by using an incident angle θ having a large power PW, based on an experimental result of the power PW of the near-field light 20l. Because of this, more suitable inspection can be performed.

Moreover, for a plurality of kinds of specifications of the concave-convex pattern 74, inspection can be performed by using such an incident angle θ that leads to a totally large power PW based on experimental results of the power PW of the near-field light 20l. At that time, as the state in which the power PW as a whole becomes large, a state, such as, a state in which the average power PW for a plurality kinds of specifications becomes large, or a state in which each of the power PW for a plurality kinds of specifications becomes uniform (for example, the standard deviation become small), may also be used.

A flowchart for the above-described operations is illustrated as follows.

Figure 7A:
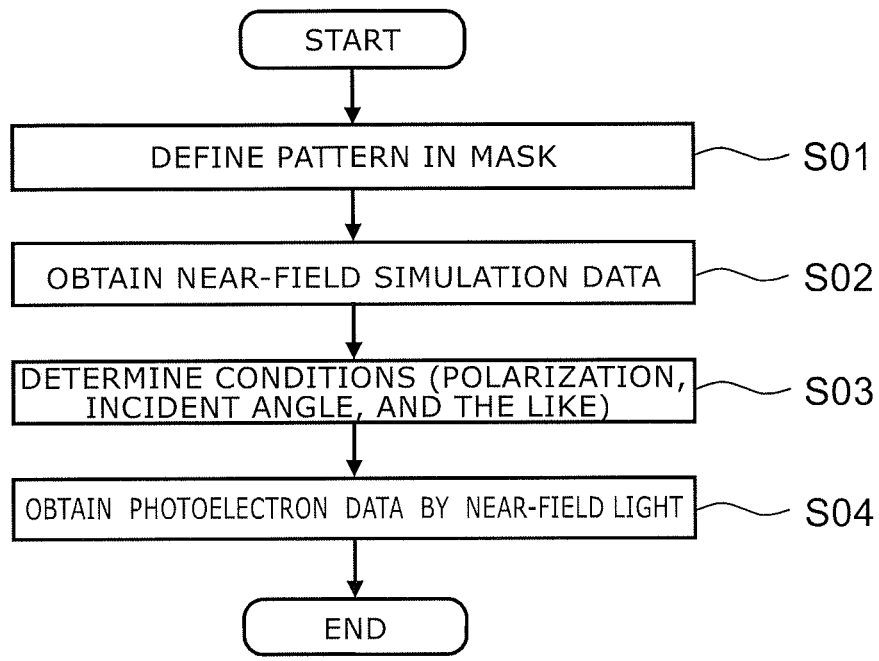
FIGS. 7A and 7B are flowchart views illustrating operations of the mask inspection apparatus according to the first embodiment.
Figure 7B:
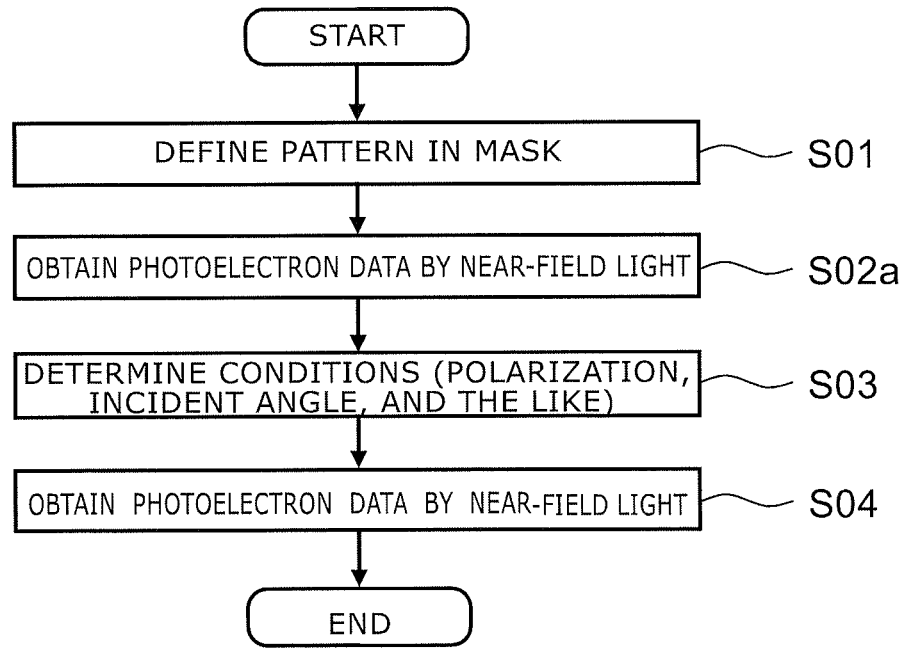

FIGS. 7A and 7B are flowchart views illustrating operations of the mask inspection apparatus according to the first embodiment.

As shown in FIG. 7A, the pattern in a mask is defined (Step S01). Then, near-field simulation data is obtained (Step S02). Based on the result, conditions (for example, polarization, an incident angle, etc.) are determined (Step S03). Then, data of the photoelectrons 70e due to the near-field light 20l is obtained by using the conditions (Step S04).

Furthermore, as shown in FIG. 7B, when determining conditions, the data of the photoelectrons 70e is obtained from a preliminary experiment (Step S02a). Then, Step S03 and Step S04 are performed based on the data.

Because of this, since the influence of a diffraction limit can be prevented by detecting photoelectrons 70e via the near-field light 20l, inspection of a fine pattern can be performed by using a low cost light source such as a UV light source, enabling to achieve a low cost mask inspection apparatus. Since high sensitivity defect inspection can be achieved, as a result, yield of devices to be produced can be improved, thereby enabling improvement of productivity. For a case in which a plurality of fine patterns are provided on the mask 70, high sensitivity defect inspection can also be achieved by the configuration described above.

One example of the operation for Die to die comparison checking mode in the mask inspection apparatus according to the embodiment 110 will now be described.

Figure 8:
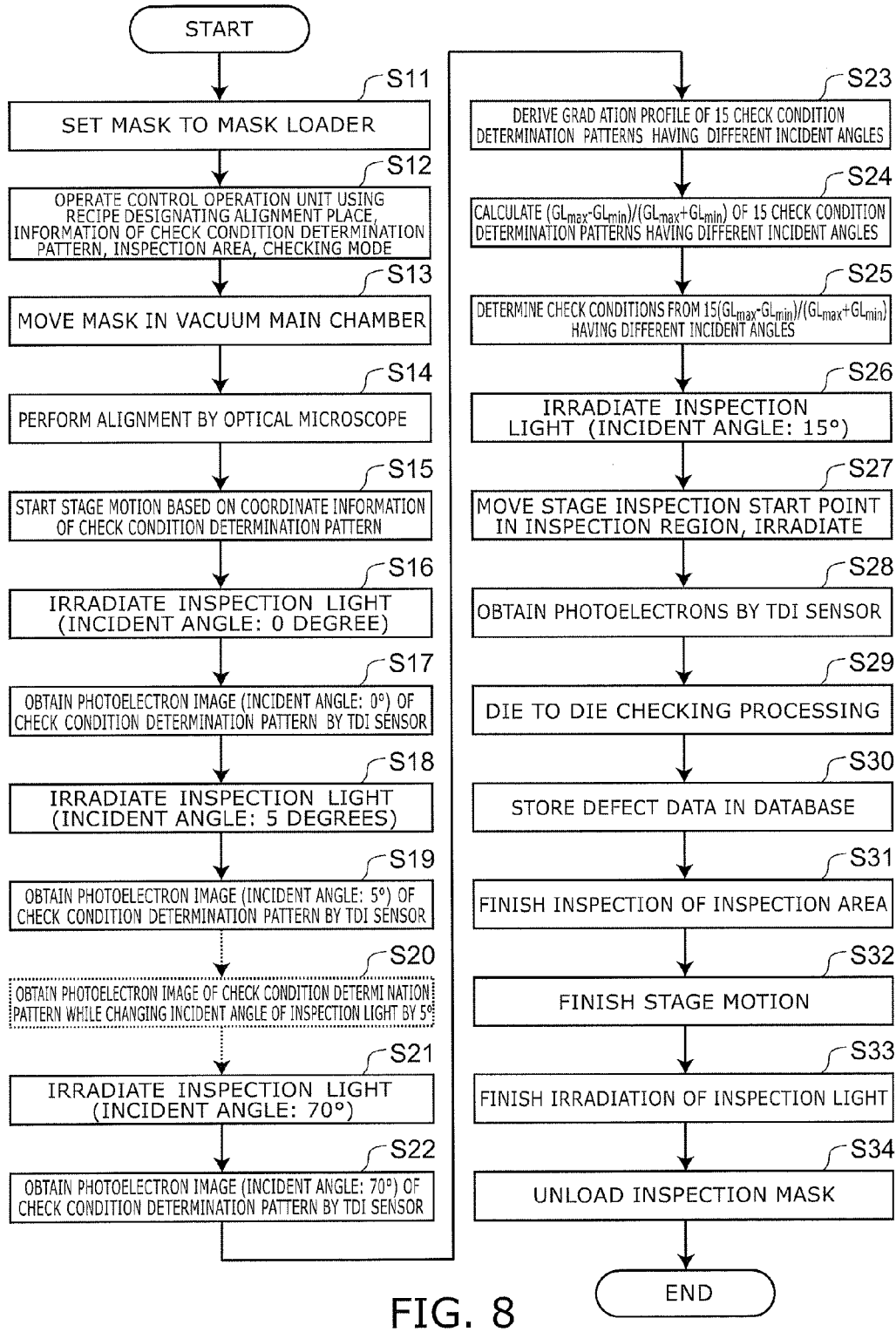
FIG. 8 is a flowchart view illustrating the operations of the mask inspection apparatus according to the first embodiment.

FIG. 8 is a flowchart view illustrating the operations of the mask inspection apparatus according to the first embodiment.

Figure 9:
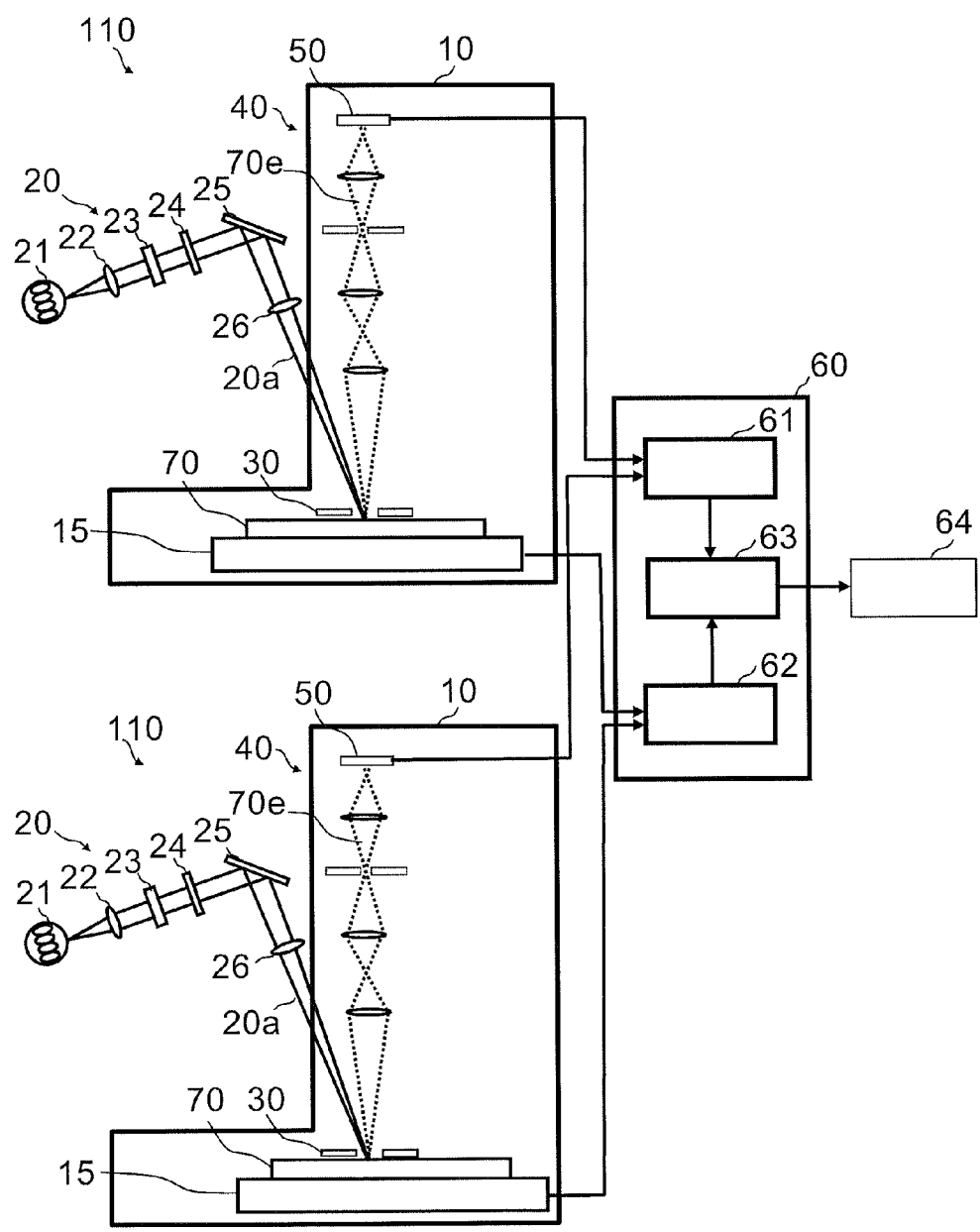
FIG. 9 is a schematic view illustrating the configuration of the mask inspection apparatus according to the first embodiment.

FIG. 9 is a schematic view illustrating the configuration of the mask inspection apparatus according to the first embodiment.

FIGS. 10A to 10D are schematic views illustrating the operations of the mask inspection apparatus according to the first embodiment.

The FIG. 10A illustrated the image of the photoelectrons 70e. FIGS. 10B to 10D are schematic views illustrating the values of characteristics obtained from the image of the photoelectrons 70e.

As shown in FIG. 9, the controller 60 is provided with, for example, a comparison logic circuit 61, a stage controller 62, and a control calculation unit 63. In this case, photoelectrons 70e are detected in a check condition determination pattern for determining check condition and a pattern in a region to be inspected. These patterns are provided on the major surface 70a of the mask 70.

As shown in FIG. 8, the mask 70 of an object to be inspected is set to a mask loader of the mask inspection apparatus 110 (Step S11).

The mask inspection apparatus 110 is operated by a control operation unit by using a recipe in which an alignment part, check condition determination pattern information, an inspection area, a checking mode, etc. are designated (Step S12).

For example, mask loading is performed by the stage controller and the mask 70 is moved into the main chamber (decompression chamber 10). Then, the mask 70 is disposed on the X-Y stage (holder 15) in the main chamber (Step S13).

For example, alignment by an optical microscope is performed, and the mask position is adjusted (Step S14) by using an alignment pattern provided at the circumference mark part 70p on the mask 70.

Stage operation is started based on coordinate information on the check condition determination pattern information (Step S15).

The irradiation of inspection light (light 20a) is performed (Step S16). The incident angle θ at this time is, for example, 0°. The wavelength λ of light 20a is, for example, 257 nm. Light 20a passes through, for example, a wave plate 24, and has a TM polarization component.

The image of photoelectrons 70e (incident angle θ=0°) of the check condition pattern is obtained by the detector 50 (for example, a TDI sensor) (Step S17).

The irradiation of the inspection light is performed while setting the incident angle θ to 0°. The image of photoelectrons 70e (incident angle θ=5°) of the check condition pattern is obtained by the TDI sensor (Step S19).

Hereinafter, in the same way, the image of photoelectrons 70e of the check condition determination pattern is obtained by changing the incident angle θ to 70° in steps of, for example, 5° (Steps S20, S21 and S22).

Then, as described above, a gradation profile of each of 15 photoelectron images obtained by changing the incident angle θ regarding the check condition determination pattern is derived (Step S23).

For example, suppose a case in which belt-like line parts 70l and space parts 70s are extended along the Y-axis and aligned along the X-axis as the concave-convex pattern 74 of the mask 70.

At this time, as illustrated in FIG. 10A, in the image 51i of photoelectrons 70e, line part images 51l corresponding to the line parts 70l and space part images 51s corresponding to the space parts 70s are obtained.

As shown in FIG. 10B, a gradation profile 53 can be obtained regarding the image 51i of photoelectrons 70e for one incident angle θ. The gradation profile 53 is, for example, the relationship between a position along the X-axis and a gradation GL (index of the brightness of an image) of the image 51i of photoelectrons 70e.

As shown in FIG. 10C, the maximum value $GL_{max}$ and the minimum value $GL_{min}$ of the gradation GL are obtained from the gradation profile 53 illustrated in FIG. 10B.

The maximum value $GL_{max}$ and the minimum value $GL_{min}$ of the gradation GL are obtained for each of the different incident angles θ.

Then, as shown in FIG. 10D, gradation characteristic value GLP $(=(GL_{max}-GL_{min})/(GL_{max}+GL_{min}))$ is calculated as one of the characteristic values regarding the gradation profile 53 (Step S24 in FIG. 8). The gradation characteristic value GLP is calculated for each of the different incident angles θ. In this example, the gradation characteristic values GLP for incident angles θ of 0°, 5°, 10°, 15°, 20°, 25°, (omitted), 55°, 60°, 65° and 70°, are 0.4, 0.5, 0.7, 0.9, 0.8, 0.7, (omitted), 0.5, 0.4, and 0.3 and 0.1, respectively.

From these results, the incident angle θ when the gradation characteristic values GLP (in this example $(GL_{max}-GL_{min})/(GL_{max}+GL_{min})$) become the maximum value, is obtained as 15°. Then, the condition is determined as the check condition (Step S25 in FIG. 8).

Then, the irradiation of the inspection light for the determined incident angle θ (=15°) is started (Step S26 of an FIG. 8). Specifically, the incident angle θ is set to 15°, the stage is moved to the inspection starting point in a region to be inspected, then the region is irradiated with the inspection light (Step S27). The image of photoelectrons 70e obtained by the inspection light is acquired by the TDI sensor (Step S28).

Various kinds of data in the check condition determination pattern and the data of photoelectrons 70e (inspection image) in the region to be inspected are stored in a data storage unit. The data storage unit is provided, for example, inside the controller 60 or outside the controller 60.

The inspection image data obtained as mentioned above, is compared with, for example, inspection image data obtained from the same pattern portion of a die neighboring to the region to be inspected (Step S29). The comparison is performed by, for example, the comparison logic circuit 61 provided to the controller 60. As a result of the comparison, places where difference is confirmed, are extracted as defects.

Information regarding the defects together with, for example, coordination information of the places of defects obtained from the stage (holder 15) is stored in the data storage (database) (Step S30). The coordinate information is acquired by the stage controller 62. Stored data of inspection information is transferred to a computer that is a data server. For example, as defect information 64 of the mask of the object to be inspected, coordinate information of defects (defect positions in the mask) and defect images are transferred. These operations are performed by, for example, the control calculation unit 63 of the controller 60. As a result of the above mentioned operations, the controller 60 outputs the defect information 64 (information regarding defects, containing the coordinate information of defect places).

Inspection of the inspection area is finished (Step S31), operations of the stage is finished (Step S32), and the irradiation of the inspection light is finished (Step S33). Then, the mask 70 of the object to be inspected is unloaded by the stage controller (Step S34), and the mask inspection is finished.

For example, a threshold value is set to a signal of difference between the signal of the defect place and the signal of the reference place. Then, when a difference signal is greater than the threshold value, the place is determined as a defect, and thus defect detection is performed. When a defect is detected by the mask inspection apparatus, repairing of the defect and cleaning of the mask are performed, based on the obtained defect information 64. After that, a loop in which mask inspection is performed again, and if a defect is detected, repairing of the defect and cleaning of the mask are performed again, is repeated until no defect is detected (no difference signal greater than the threshold value appears). Then, when no defect is detected, the mask becomes a usable state, and, for example, the mask is delivered.

Like in the case of the above-described Die to die comparison checking, Cell to cell comparison checking can also be performed.

Hereinafter, as another operation of the mask inspection apparatus 110 according to the embodiment, one example of Die to database comparison checking will be described.

Figure 11:
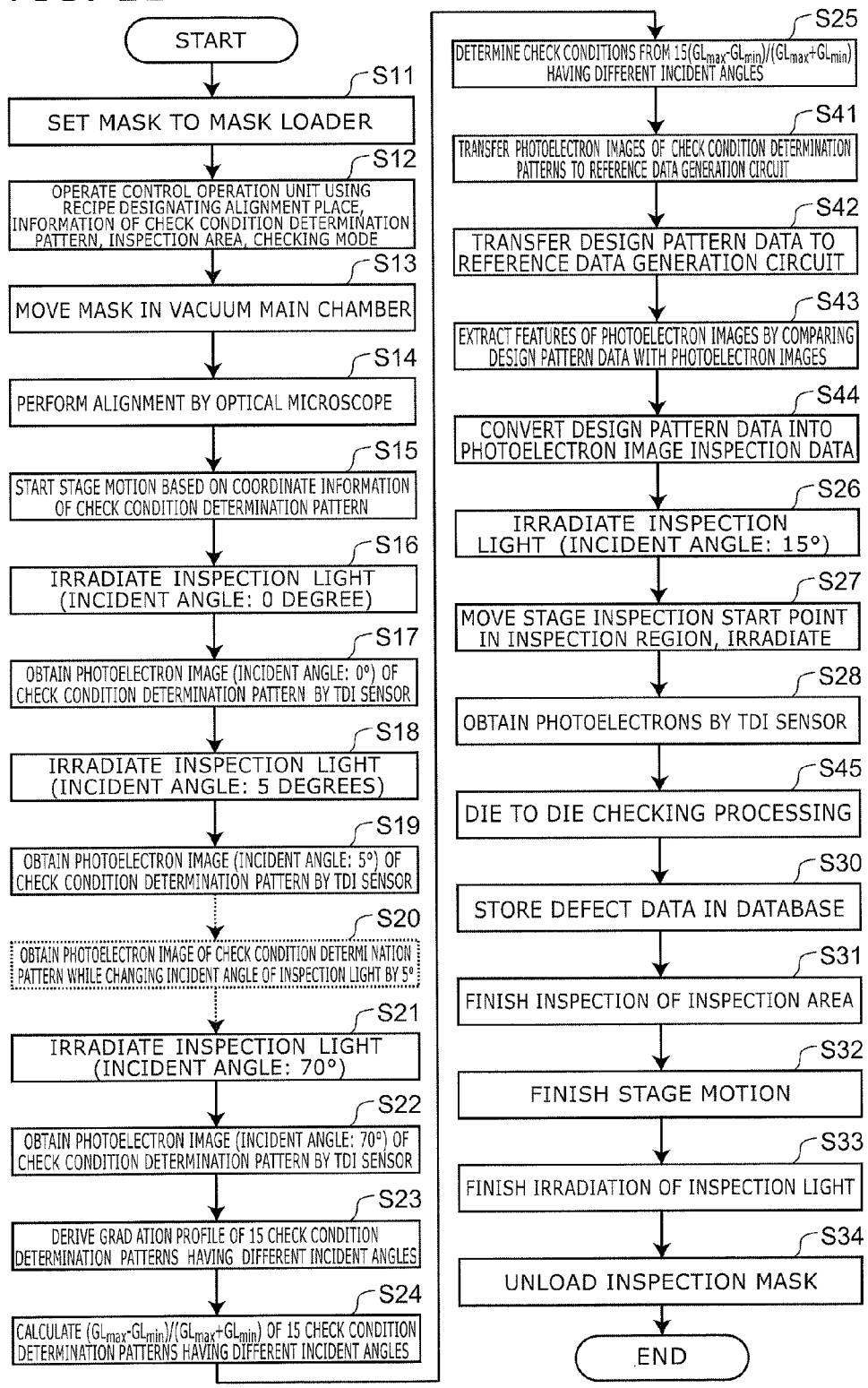
FIG. 11 is a flowchart view illustrating another operation of the mask inspection apparatus according to the first embodiment.

FIG. 11 is a flowchart view illustrating another operation of the mask inspection apparatus according to the first embodiment.

Figure 12:
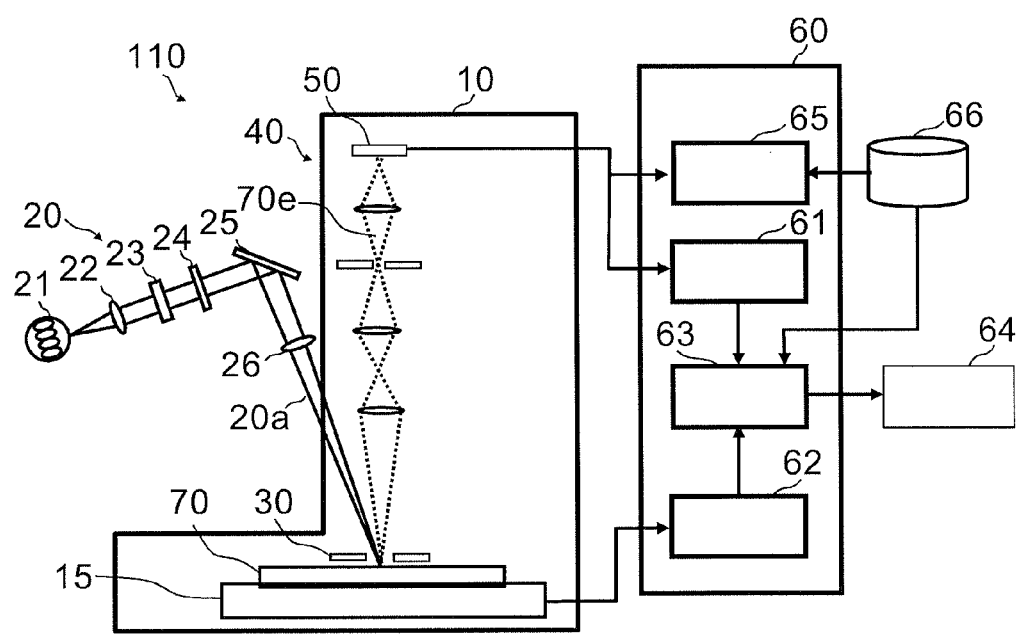
FIG. 12 is a schematic view illustrating another operation of the mask inspection apparatus according to the first embodiment.

FIG. 12 is a schematic view illustrating another operation of the mask inspection apparatus according to the first embodiment. As shown in FIG. 12, in the example, a reference data generation circuit 65 is further provided to the controller 60. Furthermore, database 66 (data storage unit) is connected to the controller 60. The database 66 may be included in the controller 60.

As shown in FIG. 11, since operation of Step S11 to Step S25 can be the same as the operation described with reference to FIG. 8, description thereof is omitted. However, in this example, a check condition determination pattern including coordinates and images prepared in advance is provided at six places on a mask. The check condition determination pattern includes information regarding the six places. Then, in Step S15, based on this information, a stage is moved to the position of the check condition determination pattern.

Also in this case, an incident angle θ when a gradation characteristic value GLP (in this example, ($GL_{max}$−$GL_{min}$)/($GL_{max}$+$GL_{min}$)) becomes the maximum value is also obtained. The incident angle θ at this time is, for example, 15°. The condition is determined as a check condition (Step S25).

In the example, image data of photoelectrons 70e of check condition determination patterns of six places obtained at the incident angle θ (=15°) is transferred to the reference data generation circuit 65 of the controller 60 (Step S41).

Then, design pattern data is transferred to the reference data generation circuit 65 from the database 66 (Step S42).

Then, comparison of design pattern data with the image data of photoelectrons 70e is performed to extract features of the images of photoelectrons 70e (Step S43). The operation is executed by, for example, the reference data generation circuit 65.

Then, using the obtained features, the design pattern data is changed into photoelectron image check data for reference (Step S44). For example, the data is saved.

Then, in the same way as the way described with reference to FIG. 8, Steps S26 to S28 are performed. That is, the image of the photoelectrons 70e obtained by light 20a with the determined incident angle θ (=15°) is acquired by the TDI sensor to obtain a check image.

Then, Die to database comparison processing for comparing the obtained check image and the photoelectron image check data for reference is performed (Step S45). Then, places where difference between them is identified, are defined as defects. Then, information regarding the defects is stored in the database 66 (data storage unit) together with coordinate information of places of defects (Step S30). After that, Steps S31 to S34 are performed, and the mask inspection finishes.

Although, examples described with reference to FIG. 8 to FIG. 12 are cases in which an incident angle θ is made suitable as a check condition, any check condition is made suitable in the embodiment. For example, one example of a case in which the wavelength λ of irradiation light 20a is made suitable, will now be described.

Figure 13:
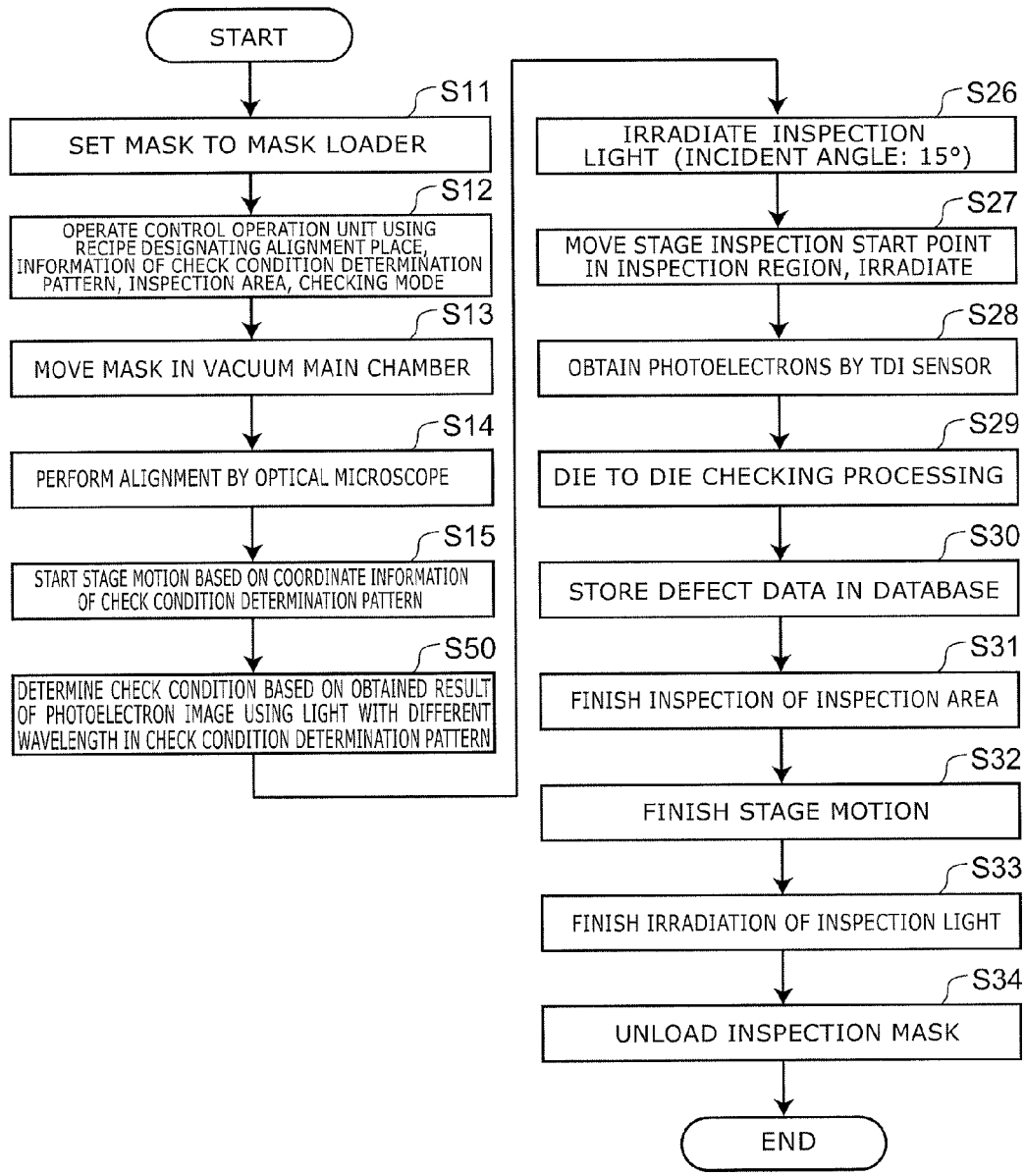
FIG. 13 is a flowchart view illustrating another operation of the mask inspection apparatus according to the first embodiment.

FIG. 13 is a flowchart view illustrating another operation of the mask inspection apparatus according to the first embodiment.

As shown in FIG. 13, after carrying out Steps S11 to S15 similarly to FIG. 8, in a check condition determination pattern, a photoelectron image is obtained by using light with a different wavelength, and the check condition is determined based on the result (Step S50). Then, the irradiation of inspection light is performed by using a defined check condition (Step S26). After that, Steps S27 to S34 are executed like in the case of FIG. 8 to carry out Die to die comparison checking.

Figure 14:
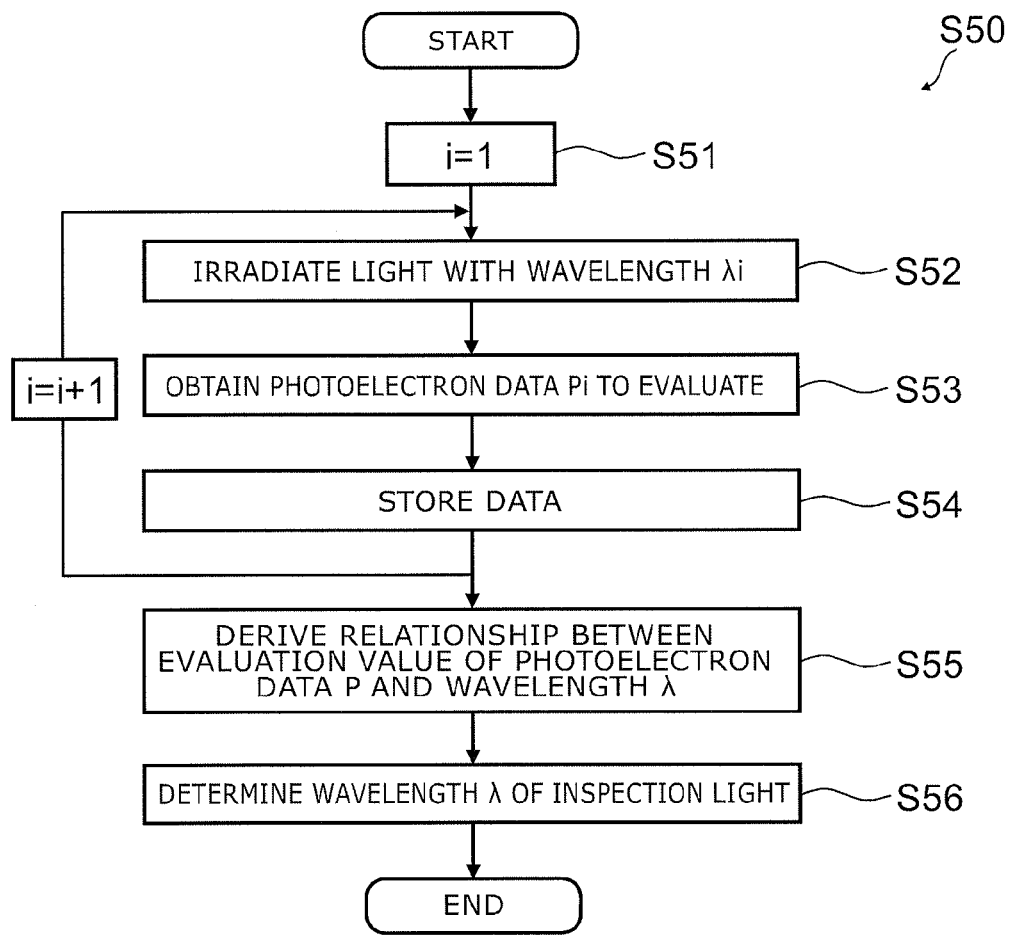
FIG. 14 is a flowchart view illustrating another operation of the mask inspection apparatus according to the first embodiment.

FIG. 14 is a flowchart view illustrating another operation of the mask inspection apparatus according to the first embodiment.

That is, FIG. 14 shows one example of the above-described step S50.

FIGS. 15A to 15C are schematic views illustrating another operation of the mask inspection apparatus according to the first embodiment.

In this example, n beams of light (n is an integer not less than two) each having a wavelength different from each other are used as light 20a. Each of the plurality of beams of light has a wavelength $\lambda i$ (i is an integer) different from each other.

As shown in FIG. 14, the integer i is set to be one (Step S51). Then, the irradiation of the light having i-th wavelength $\lambda i$ is performed (Step S52). Then, photoelectron data Pi of i-th photoelectron 70e is acquired, and the data Pi is evaluated (Step S53).

For example, as shown in FIG. 15A, the maximum value $GL_{max}$ and the minimum value $GL_{min}$ of the gradation GL are calculated from the gradation profile 53 obtained from the photoelectron data Pi. Then, the gradation characteristic value GLP for the wavelength λi is derived. As the gradation characteristic value GLP, for example, $(GL_{max}-GL_{min})/(GL_{max}+GL_{min})$ is calculated.

As shown in FIG. 14, the obtained data (for example, the gradation characteristic value GLP) is stored (Step S54).

That is, for example, as illustrated in FIG. 15B, an evaluation value (for example, the gradation characteristic value GLP) for each wavelength is stored as data.

After that, processing of i=i+1 is performed and the process returns to step S52. The above described steps S52 to S54 are performed repeatedly, at a wavelength λ(i+1) different from the wavelength λi. For example, the wavelength is changed to be 199 nm (i=1), 257 nm (i=2), 266 nm (i=3), 355 nm (i=4), 532 nm (i=5), 1064 nm (i=6), 488 nm (i=7), 514 nm (i=8), and 633 nm (i=9).

Then, if steps S52-S54 regarding the n-th procedure are performed, the relationship between the evaluation value (for example, gradation characteristic value GLP) of the photoelectron data P and the wavelength λ will be derived (Step S55).

For example, as illustrated in FIG. 15 (c), the relationship between the wavelength λ and the gradation characteristic value GLP is represented by GLP=f(λ) as a suitable function. Then, for example, a wavelength at which the gradation characteristic value GLP becomes the largest, is obtained.

Then, as shown in FIG. 14, the wavelength λ of inspection light is determined. That is, the wavelength at which the gradation characteristic value GLP becomes the largest is chosen as the wavelength of the inspection light. Or, a wavelength near the wavelength at which the gradation characteristic value GLP becomes largest, is chosen as the wavelength of the inspection light, for example.

In this manner, step S50 is performed, a check condition is defined and the above described steps are performed according to the defined conditions. Because of this, for example, high sensitivity inspection can be performed.

In the same way, cell to cell comparison checking and Die to database comparison checking can also be performed.

Thus, in this example, in the light irradiation unit 20 a mask 70 can be irradiated with a plurality of beams of light 20a having wavelengths different from each other. In addition, by being irradiated with light 20a having a suitable wavelength depending on the characteristics of the mask 70, the mask can be inspected with a higher sensitivity than ever. For example, the light irradiation unit 20 has a first operation mode in which the wavelength of light 20a is a first wavelength, and a second operation mode in which the wavelength of light 20a is a second wavelength different from the first wavelength. Furthermore, the light irradiation unit 20 may have not less than three operation modes, in which the wavelengths of light 20a are different from each other. Because of this, the above-described operation is can be achieved.

When changing the wavelength, for example, a light source may be changed. For example, by providing a plurality of light sources emitting light having wavelengths different from each other, a light source emitting light having a suitable wavelength can be used. Moreover, light having a desired wavelength may be taken from light having a plurality of peak wavelengths by using, for example, a filter etc.

In Die to die comparison checking mode (Cell to cell comparison checking mode) and Die to database comparison described above, a check condition was determined by using the check condition determination pattern and using the incident angle θ and the wavelength λ of irradiation light as parameters. However, the embodiment is not limited to this, the check condition may be determined by using the check condition determination pattern and using, for example, at least one of the illumination shape, the number of apertures, and the direction of polarization of the irradiation light.

Furthermore, although when determining the check condition (for example, the incident angle θ, the wavelength λ, and the various conditions described above), in the case described above, the check condition is determined by using the gradation characteristic value $GLP=(GL_{max}-GL_{min})/(GL_{max}+GL_{min})$ as an index, the embodiment is not limited to this. For example, as the gradation characteristic value GLP used when the check condition is determined, values regarding detected photoelectrons 70e, such as, for example, $(GL_{max}-GL_{min})/GL_{min}$, the S/N ratio of 51l of the line part images, the S/N ratio of 51s of space part images, and the maximum value of defect signals of the obtained photoelectron 70e image, may be used. In the embodiment, as described above, the check condition can be determined by using any gradation characteristic value GLP as an index.

Moreover, in the embodiment, inspection may be performed by using one check condition, or using a plurality of check conditions. For example, when inspecting one mask 70, a defect may be determined based on an inspection result using at least one of a plurality of incident angles θ and a plurality of wavelengths λ.

Figure 16:
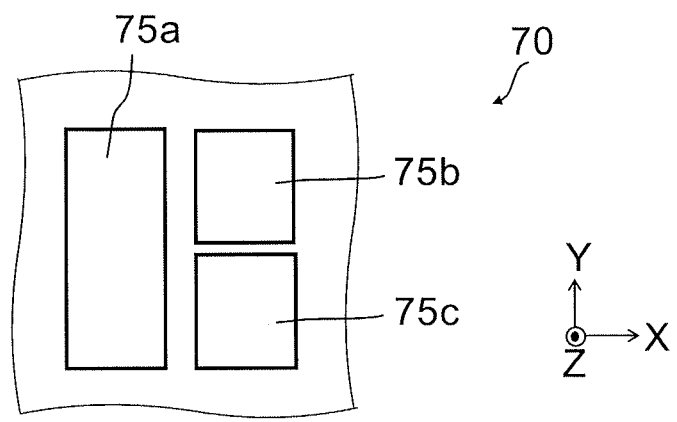
FIG. 16 is a schematic plan view illustrating the configuration of a mask inspected by the mask inspection apparatus according to the first embodiment.

FIG. 16 is a schematic plan view illustrating the configuration of a mask inspected by the mask inspection apparatus according to the first embodiment.

As shown in FIG. 16, in the mask 70 being an object to be inspected, in some cases, a plurality of regions (for example, a first region 75a, a second region 75b, and a third region 75c, etc.) may be provided. For example, in the first to third regions 75a to 75c, pitches (for example, half pitches hp) differ from each other. Furthermore, for example, shapes of patterns may be different from each other in different regions. For example, the first region 75a may have a pattern of lines and spaces, and the second region 75b may have a pattern of holes.

At this time, inspection may be performed for different regions using different check conditions.

For example, the incident angle θ in the second region 75b differs from the incident angle θ in the first region 75a. Moreover, the polarization property in the second region 75b may be changed from the polarization property in the first region 75a. Because of this, inspection can be performed with a higher sensitivity than ever by changing the check condition in different regions having different specification concave-convex patterns 74.

Furthermore, as described above, gradation characteristic values GLP (for example, $(GL_{max}-GL_{min})/(GL_{max}+GL_{min})$) in different regions having different specification concave-convex patterns 74 may be used as the check condition.

Moreover, check conditions (for example, incident angle θ, and wavelength λ, etc.) may be determined by providing a plurality of check condition determination patterns having a plurality of specifications in the major surface 70a of a mask 70 and using the plurality of check condition determination patterns.

Furthermore, as already described, check conditions may be determined by carrying out the near-field simulation for determining the irradiation condition of inspection light and using the simulation result of the near-field light 20l. In addition, check conditions may also be determined by estimating the image of photoelectrons 70e from the intensity of the near-field light 20l. The above-mentioned simulation may be performed by using, for example, the design data in the database 66, and check conditions may be determined based on the data.

The above operations can be controlled by, for example, the controller 60.

Figure 17:
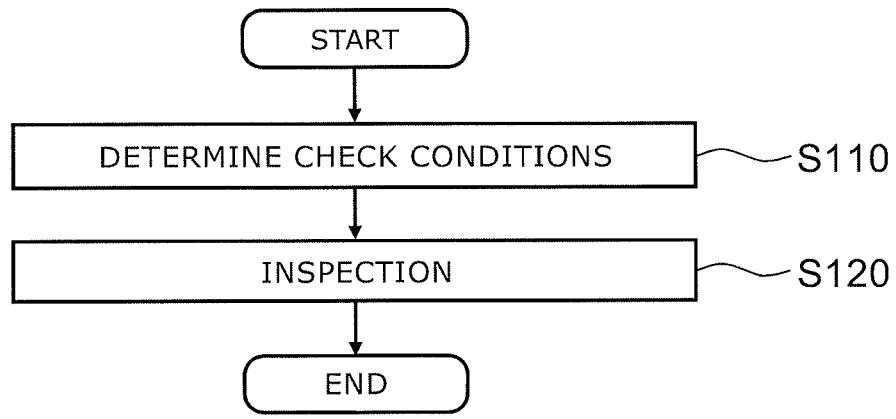
FIG. 17 is a flowchart view illustrating the operations of the mask inspection apparatus according to the first embodiment.

FIG. 17 is a flowchart view illustrating the operations of the mask inspection apparatus according to the first embodiment.

As shown in FIG. 17, the controller 60 can carry out check condition determination operation (Step S110) and inspection operation (Step S120).

In check condition determination operation, the controller 60 determines the condition of light 20*a* with which the major surface 70*a* of a mask 70 is irradiated. In the operation, for example, steps S15 to S25 illustrated in FIG. 8 and FIG. 11 are performed. In the operation, for example, step S50 (steps S51 to S56 illustrated in FIG. 14) illustrated in FIG. 13 is performed.

Then, the controller 60 carries out inspection operation based on the result of check condition determination operation. Specifically, the controller 60 compares the result of photoelectrons 70*e* generated when the mask is irradiated with light 20*a* of the determined condition with a reference value. More specifically, the controller 60 carries out, for example, steps S27 to S29 illustrated in FIG. 8 and FIG. 13. Furthermore, the controller 60 carries out, for example, steps S27, S28 and S45 illustrated in FIG. 11. Because of this, the mask 70 is inspected.

In the above described operations, the conditions of light 20*a* can include at least one of the incident angle θ of light 20*a* relative to the major surface 70*a*, the wavelength λ of light 20*a*, the polarization property of light 20*a*, the area of a region of the major surface 70*a* irradiated with light 20*a*, and the illumination shape of light 20*a*. By suitably setting such conditions, high sensitivity inspection can be achieved.

Moreover, the check condition determination operation includes determining the condition of light 20*a* so as to improve detection sensitivity of photoelectrons 70*e* using an evaluation value, based on the detection results of a plurality of photoelectrons 70*e* generated when the major surface 70*a* is irradiated with a plurality of beams of light 20*a* having different conditions and detected by the detector 50. The evaluation value is defined regarding the detected result in advance. As the evaluation value, for example, the gradation characteristic value GLP described already is used.

For example, as the evaluation value, various values regarding the detected photoelectrons 70*e*, such as, $(GL_{max}-GL_{min})/(GL_{max}+GL_{min})$, $(GL_{max}-GL_{min})$, the S/N ratio of line part images 51*l*, the S/N ratio of space part images 51*s*, and the maximum value of defect signals of the obtained photoelectron 70*e* image, are used.

High sensitivity inspection can be achieved by determining the conditions of light 20*a* so that the detection sensitivity of photoelectrons 70*e* becomes high.

When the mask 70 has a plurality of regions provided on its major surface, the controller 60 can determine the conditions of light 20*a* for the plurality of regions. Because of this, in each of the plurality of regions, high sensitivity inspection can be performed. Furthermore, the conditions of light 20*a* may be determined so that the whole of respective sensitivities (for example, the average value of the sensitivities) of concave-convex patterns 74 in the plurality of regions become high.

In the mask inspection apparatus 110 according to the embodiment, adjustment of irradiation system is simpler than a case of a conventional electron beam irradiation type mask inspection apparatus. Because of this, in the embodiment, a stable inspection image can be obtained. In addition, in the embodiment, charging of the mask 70 can be suppressed than a case in which the mask 70 is irradiated with electrons. Thereby, degeneration of images hardly occurs. Furthermore, in the electron beam irradiation type mask inspection apparatus, many noises occur because the quantity of electrons (current value) with which the mask 70 is irradiated cannot be increased. In contrast, in the embodiment, no charging occurs, thereby, the intensity of light with which the mask 70 is irradiated can be controlled arbitrarily. Because of this, the number of electrons per unit pixel of an inspection image can be increased. Thereby, noises can be reduced, enabling to detect more minute defects.

Second Embodiment

The embodiment relates to a mask inspection method. The mask inspection method includes an inspection process (for example, a process corresponding to step S120 illustrated in FIG. 17).

The inspection process includes: detecting photoelectrons 70*e* generated when the major surface 70*a* of a mask 70 disposed in a reduced pressure atmosphere is irradiated with light while guiding them with electrodes; and comparing the detection results of the detected photoelectrons 70*e* with a reference value. Specifically, for example, steps S27 to S29 illustrated in FIG. 8 and FIG. 13 are performed. Furthermore, for example, steps S27, S28 and S45 illustrated in FIG. 11 are performed. The photoelectrons 70*e* are emitted via near-field light 20*l* generated when the major surface 70*a* of the mask 70 is irradiated with light 20*a*.

According to the mask inspection method, since influence of diffraction limit can be avoided by detecting photoelectrons 70*e* via near-field light 20*l*, a fine pattern can be inspected by using a low cost light source such as a UV light source. Since high sensitivity defect inspection is possible, as a result, yield of devices to be produced can be improved, thereby enabling to improve productivity.

It is desirable for the mask inspection method according to the embodiment to further include a check condition determination process. The check condition determination process is a process of determining the conditions of light 20*a* with which the major surface 70*a* is irradiated in an inspection process, and it corresponds, for example, to step S110 illustrated in FIG. 17.

The conditions of light 20*a* can include at least one of the incident angle θ of light 20*a* relative to the major surface 70*a*, the wavelength λ of light 20*a*, the polarization property of light 20*a*, the area of a region of the major surface 70*a* irradiated with light 20*a*, and the illumination shape of light 20*a*.

Furthermore, the check condition determination operation includes determining the condition of light 20*a* so as to improve detection sensitivity of photoelectrons 70*e* using an evaluation value, based on the detection results of a plurality of photoelectrons 70*e* generated when the major surface 70*a* is irradiated with a plurality of beams of light 20*a* having different conditions and detected by the detector 50. The evaluation value is defined regarding the detected result in advance. As the evaluation value, for example, the gradation characteristic value GLP etc. described already is used.

Because of this, the mask inspection method according to the embodiment detects photoelectrons 70*e* excited via near-field light 20*l* generated from light 20*a* with which the mask 70 having a concave-convex pattern 74 is irradiated.

For example, the mask inspection method can include a process in which a check condition determination pattern provided on the mask 70 is irradiated with a plurality of beams of light 20*a* having a plurality of conditions. The check condition determination pattern is a pattern for determining the condition of light 20a with which the mask 70 is irradiated.

Furthermore, the mask inspection method includes obtaining a plurality of photoelectron images based on photoelectrons 70e excited via near-field light 20l generated by each of the plurality pieces of irradiation light 20a having a plurality of conditions. Furthermore, the mask inspection method includes determining check conditions using the obtained plurality of photoelectron images. Moreover, the mask inspection method includes carrying out inspection using the determined check conditions.

The illumination shape of light 20a described above can includes at least one of normal illumination, orbicular zone illumination, quadrupole illumination, double-pole illumination, and modified illumination. The mask inspection method can include the fact that the mask 70 is irradiated with beams of light 20a having different illumination shapes formed by a plurality of apertures having different aperture numbers.

Furthermore, the mask inspection method includes generating light 20a of at least any of TM polarized light, TE polarized light, and elliptically polarized light (including circularly polarized light) through the use of a polarization control member (for example, a polarizing element 23) provided between a light source 21 generating the light 20a and a mask 70, and causing the mask 70 to be irradiated with the generated light 20a. As the polarization control member, a plurality of optical elements having different polarization properties can be used. Because of this, the mask 70 can be irradiated with one beam of light 20a having one polarization property, or combination of a plurality of beams of light 20a with a plurality of polarization properties. High sensitivity inspection can be achieved by suitably controlling the polarization properties.

Furthermore, the mask inspection method according to the embodiment includes, for example, a first process of obtaining photoelectron images of photoelectrons 70e excited via near-field light 20l generated from irradiation light 20a by causing an concave-convex pattern 74 to be irradiated with light 20a of wavelength λ. The mask inspection method can furthermore include a second process of obtaining a plurality of photoelectron images by repeating the first process in desired times while changing the wavelength λ of the irradiation light 20a. In addition, the mask inspection method can furthermore include a third process of determining the wavelength of inspection light using a plurality of combinations of the wavelength λ of the irradiation light 20a and the corresponding photoelectron image. One or a plurality of wavelengths of the inspection light are determined in the third process. The mask inspection method can further include a fourth process of inspecting the mask 70 by causing the mask to be irradiated with inspection light of the wavelength determined in the third process.

Furthermore, the mask inspection method according to the embodiment may further include a process of dividing the major surface 70a of the mask 70 into a plurality of regions, and a process of arranging a check condition determination pattern to each of the divided plurality of regions. Then, conditions of light 20a can be determined for each of the plurality of regions. Because of this, high sensitivity inspection can be performed in each of the plurality of regions. Moreover, the conditions of light 20a may be determined so that the whole of respective sensitivities of concave-convex patterns 74 in the plurality of regions become high.

In the mask inspection method, by using images of photoelectrons 70e excited by near-field light 20l on the mask 70, resolution higher than the resolution in case of conventional optical inspection using image formation of reflection light, can be achieved, enabling to detect defects of a pattern shape with a high sensitivity, especially in case of a fine pattern.

According to the embodiment, the mask inspection apparatus and the mask inspection method capable of inspecting a fine pattern mask with a high sensitivity, are provided.

Hereinabove, exemplary embodiments of the invention are described with reference to specific examples. However, the invention is not limited to these specific examples. For example, one skilled in the art may similarly practice the invention by appropriately selecting specific configurations of components included in the mask inspection apparatus such as a decompression chamber, a holder, light irradiation unit, an electrode, a detection side optical unit, a detector, and a controller, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all mask inspection apparatuses and mask inspection methods practicable by an appropriate design modification by one skilled in the art based on the mask inspection apparatuses and mask inspection methods described above as embodiments of the invention also are within the scope of the invention to the extent that the purport of the embodiments of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A mask inspection apparatus comprising:
a decompression chamber; a holder provided in the decompression chamber to hold a mask;
a light irradiation unit to irradiate a major surface of the mask held by the holder with a near-field light;
a detector provided in the decompression chamber to detect electrons generated directly by patterns on the major surface of the mask irradiated with the near-field light;
an electrode provided between the holder and the detector and guiding the electrons in a direction from the holder toward the detector; and
a controller comparing a detection result of the electrons detected by the detector with a reference value.

2. The apparatus according to claim 1, further comprising an incident angle changing unit to change an incident angle of the light relative to the major surface.

3. The apparatus according to claim 1, wherein the light irradiation unit changes the incident angle of the irradiation light relative to the major surface.

4. The apparatus according to claim 1, wherein the holder can change an angle of the mask so that an angle between the irradiation light and the major surface changes.

5. The apparatus according to claim 1, wherein the light irradiation unit has a first operation mode in which a wavelength of the light is a first wavelength, and a second operation mode in which the wavelength of the light is a second wavelength different from the first wavelength.

6. The apparatus according to claim 1, wherein the irradiation light of the light irradiation unit includes a TM polarization component relative to the major surface of the mask.

7. The apparatus according to claim 1, wherein the irradiation light of the light irradiation unit includes a circularly polarized light including a TM polarization component relative to the major surface of the mask or an elliptically polarized light including the TM polarization component.

8. The apparatus according to claim 1, wherein
the controller further performs a check condition determination operation in which the light irradiation unit determines a condition of the light with which the major surface of the mask is irradiated, and
the controller compares the detection result of the electrons generated when the major surface is irradiated with the light of the determined conditions with the reference value, the detection result being detected by the detector.

9. The apparatus according to claim 8, wherein the condition of the light includes at least one of an incident angle $\theta$ of the light relative to the major surface, a wavelength of the light, a polarization property of the light, an area of a region of the major surface irradiated with the light, and an illumination shape of the light.

10. The apparatus according to claim 8, wherein the check condition determination operation includes determining the condition of the light so as to increase sensitivity of the detection of the electrons using a predetermined evaluation value regarding the detection result, based on the detection result of each of the electrons generated when the major surface is irradiated with a plurality of light beams different in the condition of the light, the detection result being detected by the detector.

11. The apparatus according to claim 8, wherein
the mask includes a plurality of regions provided on the major surface, and
the controller determines the condition of the light for each of the regions.

12. The apparatus according to claim 1, wherein the detector includes a Time Delayed Integration sensor.

13. The apparatus according to claim 1, wherein the detector detects the electrons as an image.

14. The apparatus according to claim 1, further comprising a detection side optical unit provided between the holder and the detector, the detection side optical unit including:
an objective lens provided between the holder and the detector;
an intermediate lens provided between the objective lens and the detector;
an NA aperture provided between the intermediate lens and the detector; and
a projector lens provided between the NA aperture and the detector.

15. The apparatus according to claim 1, further comprising a detection side optical unit provided between the holder and the detector, the detection side optical unit including a first aperture having a first numerical aperture and a second aperture having a second numerical aperture different from the first numerical aperture.

16. The apparatus according to claim 1, wherein a wavelength of the light is at least one of 199 nm, 257 nm, 266 nm, 355 nm, 532 nm, 1064 nm, 488 nm, 514 nm, and 633 nm.

17. A mask inspection method comprising an inspection process,
the inspection process including:
detecting electrons generated directly by patterns on a major surface of a mask disposed in a reduced pressure atmosphere irradiated with a near-field light, the electrons being guided with an electrode; and
comparing a detection result of the detected electrons with a reference value.

18. The method according to claim 17, further comprising a check condition determination process of determining a condition of the light with which the major surface is irradiated in the inspection process,
the condition of the light including at least one of an incident angle of the light relative to the major surface, a wavelength of the light, a polarization property of the light, an area of a region of the major surface irradiated with the light, and an illumination shape of the light; and
the check condition determination process including determining the condition of the light so as to increase sensitivity of the detection of the electrons using a predetermined evaluation value regarding the detection result, based on the detection result of each of the electrons generated when the major surface is irradiated with a plurality of beams different in the condition of the light, the detection result being detected by the detector.

19. The method according to claim 17, wherein Cell to cell comparison checking, Die to die comparison checking, or Die to database comparison checking, is performed depending on the reference value.

* * * * *